(12) United States Patent  
Itzhak et al.

(10) Patent No.: US 11,660,020 B2  
(45) Date of Patent: May 30, 2023

(54) METHODS AND SYSTEM FOR DETECTING PROPER CONNECTION OF A CONNECTOR IN A GAS SAMPLING LINE

(71) Applicant: Oridion Medical 1987 Ltd., Jerusalem (IL)

(72) Inventors: Gal Itzhak, Jerusalem (IL); Yosef Hay Cohen, Jerusalem (IL); Eran Linder, Jerusalem (IL); Avraham Turak, Jerusalem (IL)

(73) Assignee: ORIDION MEDICAL 1987 LTD, Jerusalem (IL)

( * ) Notice: Subject to any disclaimer, the term of this patent is extended or adjusted under 35 U.S.C. 154(b) by 895 days.

(21) Appl. No.: 16/515,589

(22) Filed: Jul. 18, 2019

(65) Prior Publication Data

US 2020/0022619 A1    Jan. 23, 2020

Related U.S. Application Data

(60) Provisional application No. 62/700,399, filed on Jul. 19, 2018.

(51) Int. Cl.
*A61B 5/097*    (2006.01)
*A61B 5/083*    (2006.01)
*G01M 3/26*     (2006.01)

(52) U.S. Cl.
CPC ........... *A61B 5/097* (2013.01); *A61B 5/0836* (2013.01); *G01M 3/26* (2013.01); *A61B 2560/0276* (2013.01); *A61B 2562/0247* (2013.01)

(58) Field of Classification Search
CPC ............ A61B 5/097; A61B 5/0836; A61B 2560/0276; A61B 2562/0247; G01M 3/26
See application file for complete search history.

(56) References Cited

U.S. PATENT DOCUMENTS

| | | | |
|---|---|---|---|
| 9,974,465 B2 * | 5/2018 | Colman | A61B 5/082 |
| 10,994,115 B2 * | 5/2021 | Peer | A61M 39/10 |
| 2011/0315757 A1 * | 12/2011 | Colman | G06K 19/0614 235/487 |
| 2017/0100058 A1 * | 4/2017 | Shapir | A61B 5/11 |

* cited by examiner

*Primary Examiner* — Mary E McManmon
*Assistant Examiner* — Andrew J Rost
(74) *Attorney, Agent, or Firm* — Shumaker & Sieffert, P.A.

(57) ABSTRACT

A gas analyzing module includes a first connector, which includes a connection detection mechanism (CDM), and is connectable to a gas sampling line via a second connector. The gas analyzing module also includes a pump, a pressure sensor and a controller. The controller controls operation of the pump and receives a signal from the CDM. When the pump is on/active, the controller measures the CDM output signal, and if the CDM output signal indicates misconnection between the first connector and the second connector, the controller switches the pump off only if a pressure measured in the gas sampling line corroborates the CDM's misconnection indication, or, if the measured pressure refutes the CDM's misconnection indication, the controller maintains the pump's on state. The gas analyzing module may be a capnography module configured for capnography. Also provided is a gas analyzing system that includes the gas analyzing module and a gas analyzer.

28 Claims, 8 Drawing Sheets

METHODS AND SYSTEM FOR DETECTING PROPER CONNECTION OF A CONNECTOR IN A GAS SAMPLING LINE

CROSS-REFERENCE TO RELATED APPLICATIONS

This application claims the benefit of priority to U.S. Provisional Application No. 62/700,399 filed Jul. 19, 2018, the disclosure of which is incorporated herein by reference in its entirety.

FIELD

The present invention generally relates to gas sampling lines for transferring gas samples (e.g., air with high concentration $CO_2$ that is exhaled by a subject) to gas analyzers (e.g., a capnograph), and more specifically to methods and system for detecting proper connection of a connector assembly in a gas sampling line.

BACKGROUND

A human respiratory cycle includes a sequence of events during which a subject inhales and exhales a given volume of air through the respiratory system. Inlet/outlet gas user interface, for example cannula tubing, face (respiration) masks, tubing adaptors, airways adaptors, and the like, used by subjects suffering from breathing problems typically include an oxygen port for delivering oxygen to them via an oxygen tube, and a $CO_2$ port for drawing $CO_2$ samples of $CO_2$ exhaled by the subject via a $CO_2$ tube. A subject connected, for example via a gas sampling line ("GSL"), to a capnograph exhales gases (e.g., mainly $CO_2$, some air, etc.) which are drawn via the GSL and into a $CO_2$ analyzing chamber in the capnograph by a $CO_2$ pump that also resides in the capnograph.

The capnograph includes a $CO_2$ port for receiving $CO_2$ samples that are drawn by the $CO_2$ pump. The capnograph's $CO_2$ port includes, or is connected to, a capnograph tube whose distal end is connected to a 'capnograph' connector (e.g., a filter line receptacle ("FLR") connector). The capnograph connector is adapted to engage with a counterpart (a 'tube') connector (e.g., a filter line connector ("FLC")) that is part of (connected to) the GSL. Proper connection of the two connectors (the capnograph connector and the tube connector) is a prerequisite to activation of the $CO_2$ pump and for the continual operation of the pump. Complying with this condition is essential to prevent $CO_2$ samples from being contaminated and/or diluted.

In some capnograph systems the status of the two connectors (for example "proper connection" or "misconnection" ("disconnected", "improper connection")) is detected based on light reflection and sensing. That is, the capnograph connector includes a light source and a light sensor, and the counterpart connector (the tube connector, or GSL's connector) includes a light reflecting surface. When the two connectors are properly engaged, light that originates from the capnograph connector is 'looped back' to its light sensor via the light reflecting surface of the counterpart connector, to thus indicate a proper connection of the connectors.

Determination, by the capnograph, when the connectors are properly connected, and therefore when to start operating the $CO_2$ pump, can be done reliably by using light samples. However, determination by the capnograph when the connectors are improperly connected or disconnected, and therefore when to switch off the $CO_2$ pump based on light samples, is sometimes unreliable, reasons being described below.

The electrical circuit generating the light, sensing the reflected light and interpreting the light samples reside in the capnograph. The aforesaid electrical circuit is, therefore, subjected to electromagnetic interferences. This means that the determination as to whether light samples indicate proper connection of the two connectors or not, may at times be false due to electromagnetic interferences. However, while erroneous indication that the two connectors are disconnected (when in fact they are properly connected and ready to start the $CO_2$ monitoring procedure) is less of a problem because the pump can wait (e.g., a few seconds) in the off state until the interference is over. However, when the $CO_2$ pump is already "on", a false connector disconnection indication would unjustifiably switch the pump off, which would interfere with the already in-progress $CO_2$ monitoring procedure.

SUMMARY

While monitoring a gas (e.g., $CO_2$) by a gas analyzer (e.g., a capnograph) is beneficial, there are drawbacks associated with the way the gas pump used to draw the gas into the gas analyzer is controlled. Therefore, the techniques of this disclosure generally relate to a gas analyzing system that is capable of reliably determining when the gas pump of a gas analyzing system should be switch off.

In one aspect, the present disclosure provides a gas analyzing module, includes a first connector that includes a light source and light sensor and is connectable to a gas sampling line via a second connector. In another aspect, the first connector and the second connector, or only one of the two connectors, includes a connection detection mechanism ("CDM") for detecting (e.g., by a controller) a connection state (e.g., "connection", "misconnection") of the two connectors. The CDM may include a mechanical device (e.g., leaf spring, coil spring, a pin-socket set, etc.), an electromechanical device, etc. The CDM may be configured to output a signal (e.g., for a controller) representing the connection state.

In another aspect, the gas module also includes a gas pump, a pressure sensor and a controller to control operation of the gas pump and light source and to measure intensity of light sensed by the light sensor. When the pump is on (active), the controller samples light while switching the light source between "on" state and "off" state. If light samples indicate misconnection between the first connector and the second connector, the controller switches the pump off only if a pressure measured in the gas sampling line corroborates (e.g., confirms) the light samples-based misconnection indication. If the measured pressure refutes the light samples misconnection indication, the controller maintains the pump's on state. Also provided is a gas analyzing system that includes the gas module and a gas analyzer.

In another aspect, the gas analyzing module is a $CO_2$ analyzing module useful for capnography; and the gas analyzing system is a capnograph monitoring system.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The description that follows provides various details of exemplary embodiments. However, this description is not intended to limit the scope of the claims but instead to explain various principles of the invention and the manner of practicing it.

The description herein extensively describes an example connection detection mechanism (CDM) which includes a light source, a light sensor and a light reflecting surface. However, this is only an example CDM, as other types of CDM may replace, or be used in conjunction with, the light connection detection mechanism.

Figure 1:
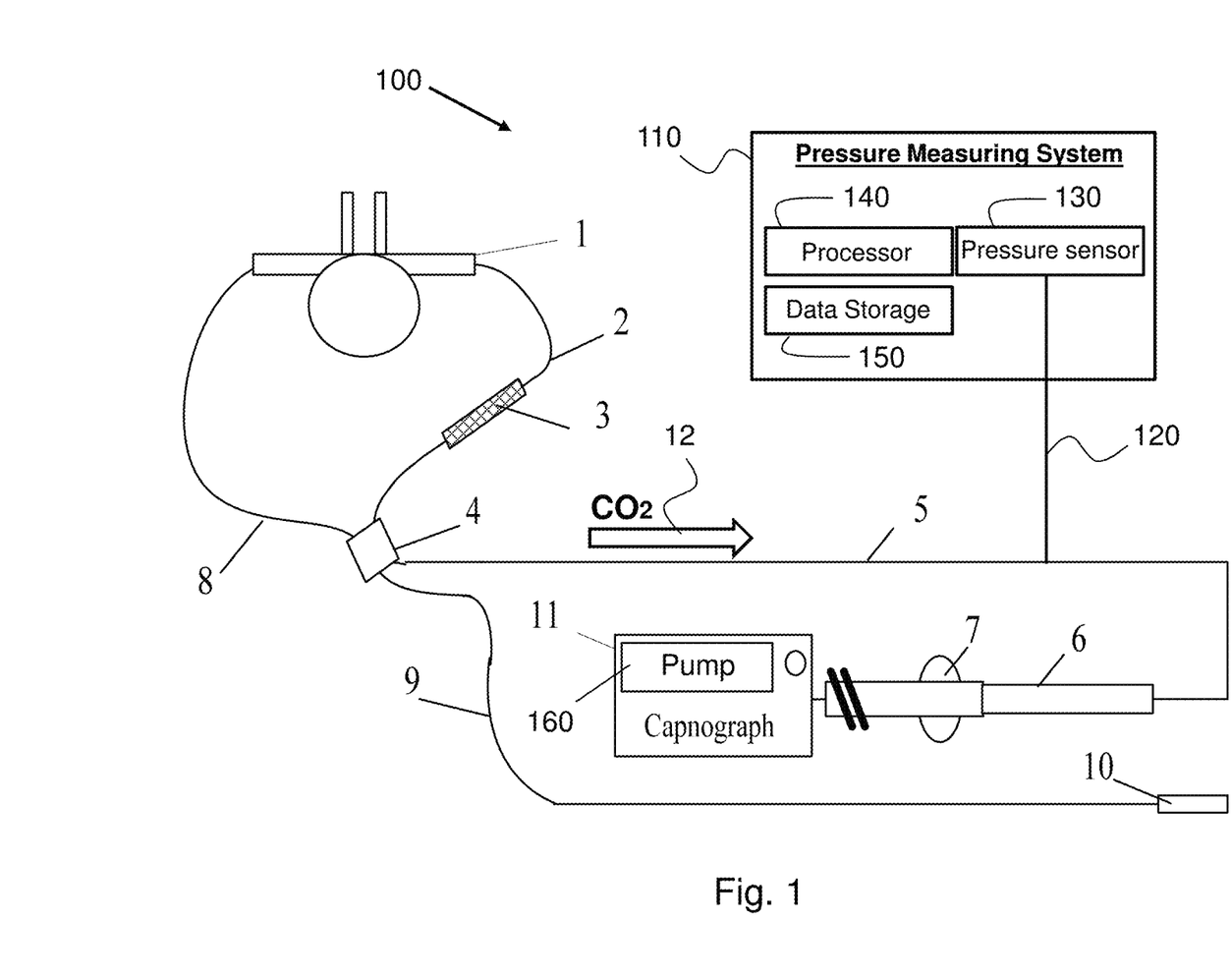
FIG. 1 is a block diagram that illustrates a $CO_2$ monitoring system setup as an example gas sampling and analyzing system.

FIG. 1 schematically illustrates a system according to an example embodiment. While the example system shown in FIG. 1 is a $CO_2$ monitoring system 100, the present invention may be applicable to any system that includes a gas sampling line.

$CO_2$ monitoring system 100 (an example $CO_2$ monitoring system) includes a cannula 1, a soft PVC tube 2, a dehumidifier 3, an oxygen-$CO_2$ tube connector 4, a soft PVC tube 5, a filter 6, a quick seal 7, a soft PVC tube 8, an oxygen tube and universal connector subassembly (9, 10), and a capnograph 11. Capnograph 11 may include a pump 160 for collecting $CO_2$ samples (12) through the gas sampling line ("GSL"). In exemplary aspects, GSL may include at least tube 5, filter 6, quick seal 7 and the tubing that connects them to pump 160 of capnograph 11. In additional exemplary aspects, filter 6 may be omitted from the GSL.

Filter 6 functions as a filter and traps liquids, and device 3 (a drying device) dehumidifies the gas samples before they reach filter 6. Dehumidifier 3 is beneficially located near cannula 1, which is the user interface through which samples of the humid gasses (including; e.g., $CO_2$) flow into the sampling tube, and filter 6 is beneficially located at the entrance of capnograph 11 to protect capnograph 11 from liquids that pass dehumidifier 3. The arrangement of filter 6 and dehumidifier 3 prevents pump 160 of capnograph 11 from being clogged by liquids (other $CO_2$ monitoring systems may include only a filter, or only a dehumidifier, or both, or none of them).

$CO_2$ monitoring system 100 may also include a pressure measuring system ("PMS") 110 for measuring a gas pressure in the GSL, for example by using a tube 120. Tube 120 may be connected to tube 5, for example via a plastic tubing manifold (the plastic tubing manifold is not shown in FIG. 1), so that tubes 5 and 120 are in gas flow communication. PMS 110 includes a pressure sensor 130, a controller 140 and a data storage device 150.

Pressure measurements made by using pressure sensor 130 may be stored in data storage device 150. Controller 140 may time pressure measurements of the gas in tube 5. For example, controller 140 may synchronize operation of PMS 110 and pump 160 such that controller 140 controls measurement of pressure of the gas in tube 5 (and processing of the pressure measurements) to take place during operation of pump 160 (rather than measuring the gas pressure in tube 5 if pump 160 is deactivated, that is, if the pump is off).

In some embodiments, PMS 110 may be separate from capnograph 11 (for example as shown in FIG. 1). In other embodiments, PMS 110 may be part of capnograph 11, for example as an integral module or unit of capnograph 11. If PMS 110 is separate from capnograph 11, controller 140 may be in communication (e.g., exchanging data, control signals, messages, etc.) with a controller operating capnograph 11. If PMS 110 is an integral module or unit of capnograph 11, a same controller (e.g., controller 140) may control the operation of both capnograph 11 and PMS 110.

In one example, PMS 110 is embedded in (e.g., integrated into) capnograph 11 and controller 140 operates both capnograph 11 and PMS 110. Also the example, capnograph 11 is "on", ready for $CO_2$ monitoring, and $CO_2$ pump 160 is currently "off", waiting until connector 7 (to which CO2 tube 5 is connected via filter 6) is properly connected to capnograph 11. In order to prevent air from contaminating the $CO_2$ measuring cell in capnograph 11 (or to minimize the adverse effect of air on the $CO_2$ measurements), $CO_2$ pump 160 should be in the "off" state (inactive) until capnograph 11 receives, or generates, an indication that indicates that connector 7 (the 'tube' connector) and the counter connector (the capnograph's connector) are properly connected. When proper connection of the two connectors is indicated, the controller activates $CO_2$ pump 160, thus commencing the $CO_2$ monitoring procedure.

Figures 2A, 2B, 2C:
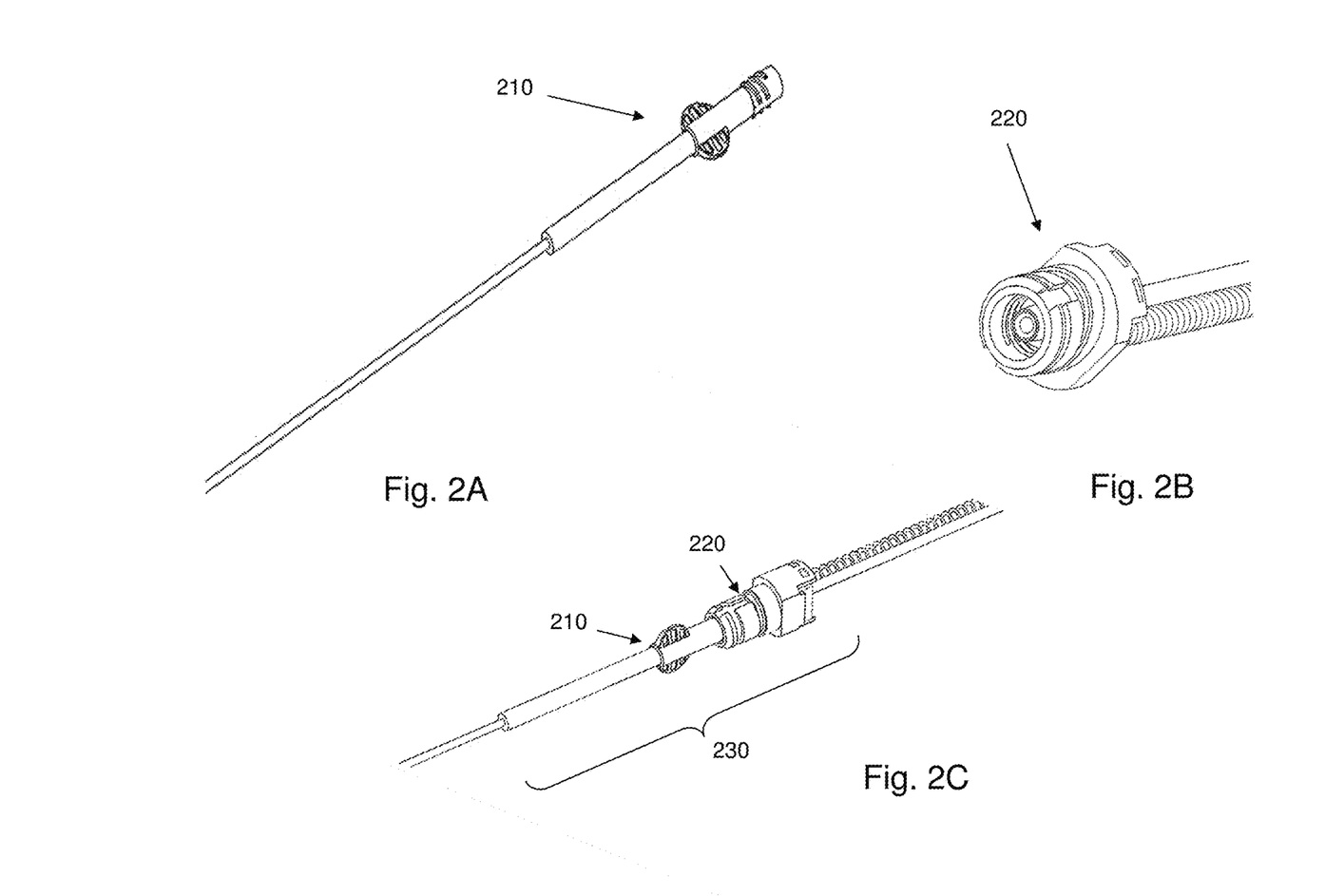
FIG. 2A is a perspective view of a tube (or GSL) connector.
FIG. 2B is a perspective view of a capnograph connector.
FIG. 2C illustrates the tube connector of FIG. 2A and the capnograph connector of FIG. 2B properly (operationally) connected.

An example of tube connector 7 is shown in FIG. 2A at 210. An example of the capnograph's connector (a counterpart connector) is shown in FIG. 2B at 220. FIG. 2C depicts a connector assembly 230 that includes the two connectors (tube connector 210 and capnograph connector 220) properly connected (properly engaged), ready for collecting $CO_2$ samples by the $CO_2$ pump of a capnograph (e.g., by capnograph pump 160).

Figure 3A:
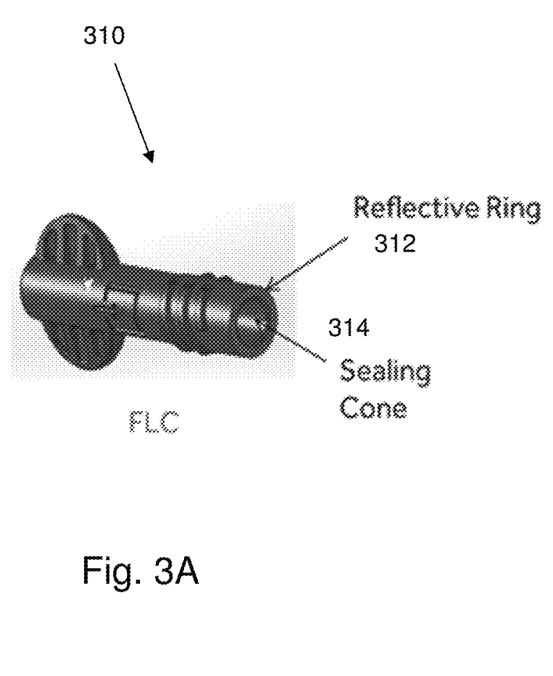
FIG. 3A is a side elevation view of a tube (or GSL) connector.
Figure 3B:
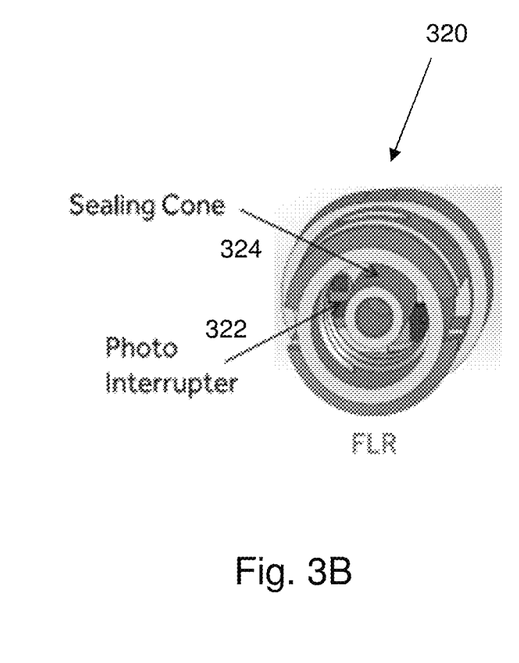
FIG. 3B is a front elevation view of a capnograph connector.

In exemplary aspects, indication of a proper connection of the two connectors may be obtained by using light signals (e.g., light samples), for example by using a tube connector that includes a light reflective surface and a capnograph connector that includes a light source. Referring to FIGS. 3A-3B, tube connector 310 (FIG. 3A) includes an example light reflective ring 312; and capnograph connector 320 (FIG. 3B) includes an example photo interrupter 322 (Photo interrupter 322 includes a light source; for example, one or more light emitting diodes ("LEDs"), and a light sensor). Briefly, when the tube connector and the capnograph connector are properly connected, the amount of light that light reflecting surface 312 reflects to the light sensor of photo interrupter 322 is relatively high, thus indicating proper connection. Tube connector 310 includes an internal sealing cone 314; and capnograph connector 320 includes an external sealing cone 324. The two sealing cones, when properly engaged, provide an airtight connection.

During operation of capnograph 11, the capnograph's controller (if PMS 110 resides or is incorporated in capnograph 11, the controller may be, for example, controller 140)

may operate the light source of photo interrupter 322, (e.g., LED(s)) that is(are) positioned in the capnograph connector, for example, in a way that the light source is alternately switched between an "off" state and an "on" state (in exemplary embodiments, controller 140 controls, alone or with another controller, the operation of both capnograph 11 and PMS 110).

Using the light sensor in the capnograph connector, light samples representing the light sensed by the light sensor at each light source operation state are collected, for example by controller 140, and saved in a data storage (e.g., data storage 150). The light sensor in the capnograph connector may sense light regardless of where the sensed light originates from, and thus is unable to distinguish between light originating from different light sources. That is, the light sensed by the light sensor in capnograph connector 320 may be: a light emitted by the light source of the capnograph connector (i.e., 'internal' light) and reflected from reflection surface 312 of tube connector 310 when the two connectors are properly (e.g., operationally) connected; or a 'partial' light reflection when the two connectors are poorly connected; or an ambient light (i.e., 'external' light; e.g., daylight, artificial light; e.g., room light) when the two connectors are not connected at all (i.e., completely disconnected). Alternating the light source, for example by controller 140, between "on" state ('light' state) and "off" state ('dark' state) solves this problem, as described herein.

When tube connector 310 and capnograph connector 320 are properly connected, the light sensed by the light sensor of capnograph connector 320 is expected to have high intensity level when the LED (or another light source for that matter) is "on", and low to zero intensity level when the LED is "off". When tube connector 310 and capnograph connector 320 are properly connected, and controller 140 switches the LED off, the intensity level of the light sensed by the light sensor in the capnograph connector is expected to be low to zero because the tube connector prevents (blocks) external light from entering through the connector assembly and reaching the light sensor (directly or indirectly). When tube connector 310 and capnograph connector 320 are properly connected (meaning that the connector assembly is operational), the connector assembly may not be completely light-tight, meaning that spacings ('gaps') between the two connectors, even if properly engaged, may still enable some external light to reach the light sensor embedded in the capnograph connector. Therefore, some low light intensity level may still be expected even when the two connectors are properly connected. To solve that problem, a light intensity margin, or a light intensity threshold value, can be used to accommodate for such 'stray' light sensing. This light sensing technique may be utilized, for example by controller 140, to determine whether the tube connector 310 and capnograph connector 320 are properly connected, as described below in more detail.

In order for controller 140 to determine, at any given time, whether the two connectors are properly connected, controller 140 may calculate, for each connection determination, one light intensity peak-to-peak ("PTP") value or a plurality of PTP values from light samples that are/were taken both in the LED's "off" state and in the LED's "on" state. By way of example, to make a connection determination, controller 140 may calculate a predetermined number of PTP values according to a PTP schedule; that is, controller 140 may calculate a predetermined number of PTP values per unit of time, or per a predetermined time interval or time cycle, or once in a while, e.g., once every few seconds (e.g., once every ten seconds), or once every few minutes (e.g., once every three minutes), etc. Controller 140 may alternately switch the light source between on and off states accordingly, by controlling the frequency and/or duty cycle of each "on/off" cycle in accordance with the PTP schedule that is to be used. Each PTP value may be obtained (calculated) from one or more light intensity values obtained during an "on" period of the light source, and from one or more light intensity values obtained during an "off" period of the light source that may temporally precede or succeed the "on" period of the light source.

Controller 140 may control the light source to alternate between "off" state, in which the light source is shut down (not emitting light), and "on" state, in which the light source emits light (for example at a predetermined or otherwise known intensity); and the difference between the intensity of the light sensed in the "off" state and the intensity of the light sensed in the "on" state (e.g., the PTP value) is expected to be large (corresponding to high PTP value) when the two connectors are properly connected. Therefore, controller 140 may check whether the PTP value is greater than the predetermined threshold value, PTP|th, and, if is greater than the predetermined threshold value, PTP|th, controller 140 may determine that the two connectors are properly connected (as described herein, low light intensities can be expected in the "off" state of the light source when tube connector 310 and capnograph connector 320 are properly connected, and high light intensities can be expected in the "on" state of the light source when the two connectors are properly connected).

Controller 140 may calculate a light PTP value ("PTP value" for short) for each "on/off" cycle (an "on/off" cycle is a light cycle including a light "on" period followed by a light "off" period, or vice versa), and base a connector connection state on each PTP value individually; e.g., a connection state determination per PTP value. Alternatively, controller 140 may calculate one (an average) PTP value for a series of light cycles (a series of light cycles may include a predetermined number of successive light cycles. By way of example, a series of light cycles may include five light cycles). If controller 140 bases a determination, regarding the connection state of the connector assembly (e.g., properly connected, or not), on a series of successive light cycles, the controller may average the "on" light samples and the "off" light samples and calculate an average PTP value for the entire series of light cycles as a difference between the average "on" light sample and the average "off" light sample. Alternatively, controller 140 may calculate a PTP value for each light cycle of the series of light cycles, to thus obtain a series of PTP values, and calculate an average PTP value for the series of light cycles by averaging the PTP values.

Controller 140 may, for example, sample light intensities one or more times during an "on" period and/or an "off" period of each light cycle of the series of light cycles; then it may calculate an average "on" light intensity value across the series of light cycles and, similarly, an average "off" light intensity value across the same series of light cycles. Then, controller 140 may calculate an average PTP value for the entire series of light cycles by, for example, calculating a difference between the calculated average "on" light intensity value and the calculated average "off" light intensity value. Alternatively, controller 140 may calculate a separate PTP value for each light cycle in a series of light cycles, thus obtaining a series of PTP values for the series of light cycles. Then, controller 140 may calculate an average PTP value for the series of light cycles from the series of PTP values. Regardless of the number of PTP values that controller 140 uses to determine a connector connection status, controller 140 may repeat calculation of the PTP, or PTPs, over time, for example until the $CO_2$ monitoring procedure ends, or until the procedure is brought to a halt (regardless of the reason).

If controller 140 determines that the PTP value is greater than the predetermined threshold value, controller 140 determines that the two connectors are properly connected. Therefore, controller 140 turns $CO_2$ pump 160 "on". The $CO_2$ pump may run (be in the "on" state) for as long as the value of the PTP, based on which the controller determines a connection state (e.g., individual PTP or an average PTP, per the discussion herein), is greater than the predetermined threshold value, or until a user of the capnograph system (e.g., health care personnel) switches $CO_2$ pump 160 off, such as when the $CO_2$ monitoring procedure ends. However, if, for example, controller 140, determines that the PTP value it uses for the determination is not greater than the predetermined threshold value, controller 140 maintains the $CO_2$ pump's "off" state.

As described herein, determining a proper (operational) connector connection only based on light samples (based on light intensity measurements) may be problematic at times due to, for example, the adverse effect that electromagnetic interferences may have on the electrical circuits involved in the light intensity measurements and/or interpretation (such effect might cause the $CO_2$ pump to be erroneously turned "off" when it should stay running; i.e., "on"). Using pressure measurements that 'backup' the light-based connector disconnection decision solves that problem. It is noted that while light samples based determination is useful in initiating pump activation, using pressure measurements is also useful when the pump is "on" and the light samples indicate, potentially erroneously, disconnection or improper connection of the tube connector and the capnograph connector (pressure measurements may not be useful when the $CO_2$ pump is off because no vacuum is created in the GSL).

Controller 140 may be also configured to detect a connector assembly connection state that is required to switch a $CO_2$ pump "off", according to an example embodiment By "controller configuration", "controller configured to", and the like, it is meant herein, for example, a controller that includes a set of instructions which, when executed by the controller, cause the controller to carry out the steps, processes, computations, determinations, pump activation and deactivation, functionalities, etc. described herein. A "configured controller" may also include peripherals, sensors, etc., from which, or to which, the controller may transfer, or receive, data, messages, control signals, etc.

In one example, $CO_2$ pump 160 is in the "on" state, for example as a result of or following any "off" state to "on" state switching steps or switching process that are(is) described herein, for example as a result of or following the "off"-to-"on" switching process that is described above. While $CO_2$ pump 160 is "on", controller 140 alternately switches the light source in the capnograph connector device between "off" state and "on" state, and, using a light sensor that is embedded in or incorporated into the capnograph connector, controller 140 may collect light samples that represent the light that is sensed by the light sensor at each light source operation state.

As described herein, the light sensor in the capnograph connector does not distinguish between light originating from different light sources; and, in addition, when the two connector devices are properly connected, the light sensed by the light sensor of the capnograph connector is expected to have high intensity when the LED (or another light source for that matter) in the capnograph connector is "on", and low to zero intensity when the LED is "off".

Controller 140 may calculate a light intensity PTP value from light samples that are/were taken both in the LED's "off" state and in the LED's "on" state (As described herein, low light intensities can be expected in the "off" state of the LED when the two connector devices are properly connected, and high light intensities can be expected in the "on" state of the LED when the connectors are properly connected). Controller 140 may control the light source to alternate between "off" state, in which the light source is shut down (not emitting light), and "on" state, in which the light source emits light, and the difference between the intensity of the light sensed in the "off" state and the intensity of the light sensed in the "on" state (e.g., the PTP value) is expected to be large (corresponding to high PTP value) when the two connectors are properly connected. Therefore, if the PTP value is high (e.g., if it is greater than a predetermined threshold value (PTP|th), controller 140 may determine that the two connectors are, or still are, properly connected, and, following this determination, controller 140 may maintain the "on" state of $CO_2$ pump 160.

$CO_2$ pump 160 may run (be in the "on" state) for as long as the PTP value is greater than the predetermined threshold value, or until a user of the capnograph system (e.g., health care personnel) intentionally switches the $CO_2$ pump off, such as when the $CO_2$ monitoring procedure ends. However, if controller 140 determines that the PTP value is not greater than the predetermined threshold value, it may be that the two connectors are improperly connected or completely disconnected, or that the light samples, processing or interpretation has been compromised (e.g., adversely affected) by electromagnetic interferences (or by some other interference; e.g., by mechanical interference). Initially, if the PTP value is not greater than the predetermined threshold value, $CO_2$ pump 160 is to be switched off due to the connector connection being allegedly inoperational. However, if the cause to the low PTP value ('low value'—a value not greater than the predetermined threshold value) is an electromagnetic interference (or another type of interference), the $CO_2$ pump's "on" state is maintained at least until the connector assembly's connection state (e.g., "proper connection", "improper connection", "complete disconnection") is reevaluated by using another, orthogonal (light independent), parameter. A suitable orthogonal parameter may be any parameter that: (1) can be used to determine the connector assembly connection status; (2) is immune to electromagnetic interferences; and (3) does not depend on light. The connector assembly's connection state reevaluation process is referred to herein as a "corroboration phase".

The corroboration phase may generally include, for example, steps involving manipulation of, for example, pressure measurements/samples in any way that can result in enhanced connection determination accuracy, etc. The corroboration phase, which uses pressure as an example orthogonal parameter, utilizes the fact that when $CO_2$ pump 160 draws $CO_2$ from (through) the gas sampling line ("GSL"), a vacuum is created in the GSL; that is, the gas pressure in the GSL gets lower than the ambient/atmospheric pressure (lower than the air/gas pressure just outside the GSL) (The GSL includes two gas tubes and the two connectors, all of which are in gas flow communication). The amount ('depth') of vacuum helps determine whether the GSL leaks, due for example to the two connectors being improperly connected or completely disconnected. In general, the better the connectors are connected, the more airtight their connection and, consequently, the 'deeper' the vacuum (the lower the pressure in the GSL relative to the air pressure outside the GSL), up to an operational vacuum limit. For example, when the pump is "on" (active) and the connectors are properly connected, the pressure in the GSL may typically be lower than the ambient pressure by approximately 30 hPa (0.03 bar) (for a standard 2-meter long and 1.0 mm inner diameter tube, and a gas flow rate of 42-65 milliliter per minute) (Other tubes and/or gas flow rates may likewise be used, and the operational vacuum limit, hence a threshold value used in the determination process, may change to accommodate these changes). On the other hand, if the pressure's drop in the GSL (relative to the ambient pressure) is less than, for example, 5 hPa, this may indicate a leakage in the connector assembly, and, therefore, improper connection of the two connectors.

If controller 140 'finds' (e.g., infers, determines) that the vacuum created by pump 160 is deep 'enough'; for example if the pressure difference between the (low) pressure in the GSL and the (e.g., atmospheric) pressure outside the GSL is greater than a threshold value (which may depend, among other things, on the internal diameter and overall length of the gas tube of the GSL), controller 140 determines that the two connectors are connected, contrary to the light based connector disconnection indication. Therefore, controller 140 maintains the $CO_2$ pump's "on" state even though the light samples indicate connectors' poor connection or disconnection. However, if controller 140 finds that the vacuum is not lower enough relative to the ambient pressure, controller 140 determines that the two connectors are disconnected, or they are improperly connected, which is in agreement with (e.g., corroborating) the initial disconnection (or poor connection) decision arrived at by controller 140 by using light samples. Therefore, controller 140 turns off $CO_2$ pump 160.

Figure 1A:
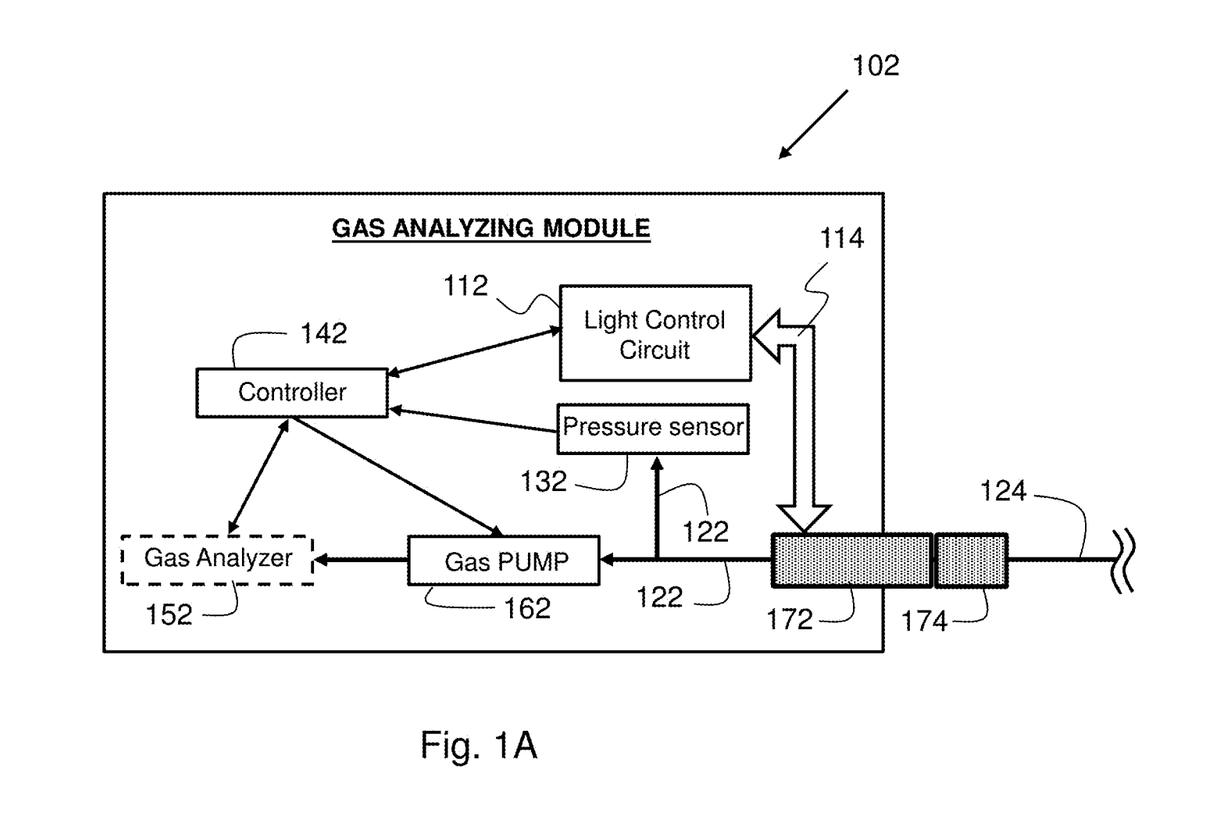
FIG. 1A is a block diagram that illustrates a gas analyzing module.

FIG. 1A shows a gas analyzing module 102 for a gas analyzing system according to an example embodiment. Gas analyzing module 102 may include a gas connector 172 to receive gas samples (for example $CO_2$ samples) from a gas sampling line 124 via a gas sampling line connector 174 of gas sampling line 124. Gas sampling line 124 may be connected to any source of gas that needs to be analyzed, for example to a cannula collecting $CO_2$ gas that is exhaled by a subject, and gas analyzing module 102 can be configured accordingly. For example, gas analyzing module 102 may be used, or adapted for use, in capnography.

Gas connector 172 includes a light source and a light sensor (Example light source and light sensor are shown in FIG. 3B). Gas analyzing module 102 may also include a pump 162 to draw $CO_2$ samples via gas connector 172 for analysis, a pressure sensor 132 to sense pressure in gas sampling line 124, and a controller 142.

Controller 142 may control operation of gas pump 162 and the light source; and it may measure intensity of light that is sensed by the light sensor. Controller 142 is configured to execute various steps related to each of the two operational states of pump 162—"on" state and "off" state. When pump 162 is on (active), controller 142 may sample light while it switches the light source between "on" and "off", and when light samples indicate misconnection between capnograph connector 172 and gas sampling line connector 174, controller 142 may switch pump 162 off when a pressure measured in gas sampling line 124 corroborates (e.g., confirms) the light samples-based misconnection. Controller 142 may use a pressure threshold value to determine corroboration, or refutation, of a connector's misconnection indication. Controller 142 may maintain pump 162 in the on state if the measured pressure refutes (e.g., negates, contradict) the light samples-based misconnection indication.

When pump 162 is off/inactive, for example when a gas monitoring procedure just commences, controller 142 may sample light while it switches the light source "on" and "off", and when light samples indicate a proper connection of capnograph connector 172 and gas sampling line connector 174, controller 142 may switch pump 162 on.

Gas analyzing module 102 may also include a light control circuit 112 to enable (for example controller 142) switching 114 of the light source between "on" and "off", and for receiving 114 a signal that represents light which is sensed by the light sensor. Gas analyzing module 102 may also include a gas analyzer 152.

Controller 142 may alternately switch the light source between "on" state and "off" state; and, using the light sensor, it may sense light one or more times during an "on" state and during an "off" state. The light sensed by the light sensor of gas connector 172 may be any one, or a combination, of: (i) light originating from the light source and reflected, at least partly, by a light reflecting surface of (e.g., embedded in, coating part of) gas sampling line connector 174; and (ii) light which is not originating from the light source (e.g., an external light; e.g., natural light, room light, etc.).

Gas pump 162 may be connected to gas connector 172 by a pump tube 122. Pressure sensor 132 may be in fluid flow communication with pump tube 122, and, via pump tube 122, with (to sense pressure in) gas sampling line 124.

Figure 1B:
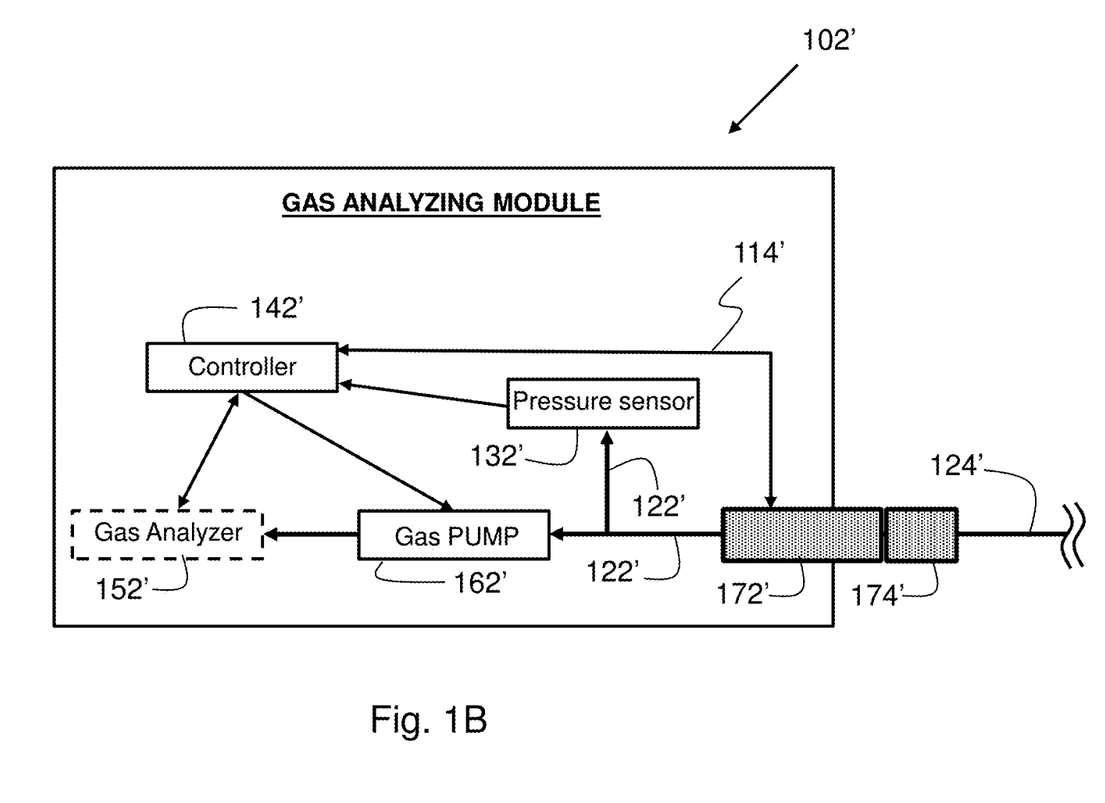
FIG. 1B is a block diagram that illustrates a gas analyzing module.

FIG. 1B shows a gas analyzing module 102' for a gas analyzing system according to an example embodiment. Gas analyzing module 102' may include a gas connector 172' to receive gas samples from a gas sampling line 124' via a gas sampling line connector 174'. Gas connector 172' may include (e.g., have embedded or contained in it, or may have attached to it) a connection detection mechanism ("CDM") to detect connection of capnograph connector 172' and gas sampling line connector 174' (the CDM is not shown in FIG. 1B). The CDM may be entirely embedded in, or attached to, gas connector 172'; or the CDM may be partly embedded in, or attached to, gas connector 172' and partly in/to gas sampling line connector 174'.

Gas analyzing module 102' may also include: a pressure sensor 132' to sense pressure in gas sampling line 124', a pump 162' to draw gas samples via gas connector 172' for analysis by a gas analyzer (for example by gas analyzer 152'), and a controller 142' to control operation of pump 162' and to determine, based on a signal 114' output by the CDM, connection or misconnection of gas connector 172' and gas sampling line connector 174'. Controller 142' is configured to, when pump 162' is on/active and CDM signal 114' indicates misconnection between gas connector 172' and gas sampling line connector 174':

(i) switch the pump off when a pressure measured by pressure sensor 162' in gas sampling line 124' corroborates the CDM's misconnection indication; and (ii) maintain the pump in the on state if the measured pressure refutes the CDM's misconnection indication.

Controller 142' is further configured to, when the pump 162' is off/inactive, read the CDM signal and, if the CDM signal indicates a proper connection of the capnograph connector 172' and the gas sampling line connector 174', to switch the pump 162' on.

Gas analyzing module 102' may further include a pump tube 122', which connects pump 162' to gas connector 172'. Pressure sensor 132' may be in fluid flow communication with pump tube 122' to sense pressure in gas sampling line 124'. Controller 142' may use a pressure threshold value, or a pressure range threshold value, to determine corroboration, or refutation, of a connector's misconnection indication. Gas analyzing module 102' may further includes a gas analyzer 152'.

In some embodiments, the connection detection mechanism (CDM) may include a light source and/or a light sensor. In other embodiments, the CDM may include a mechanical device (for example a limit switch, an electrically conductive leaf spring, coil/helical spring, metal pin, etc.), an electromechanical system, or any combination thereof, with or without a light sensing device.

Gas analyzing module 102' may be, for example, a $CO_2$ analyzing module, and the $CO_2$ analyzing module may be part of, or used with, a $CO_2$ analyzing system used in capnography.

Figure 4A:
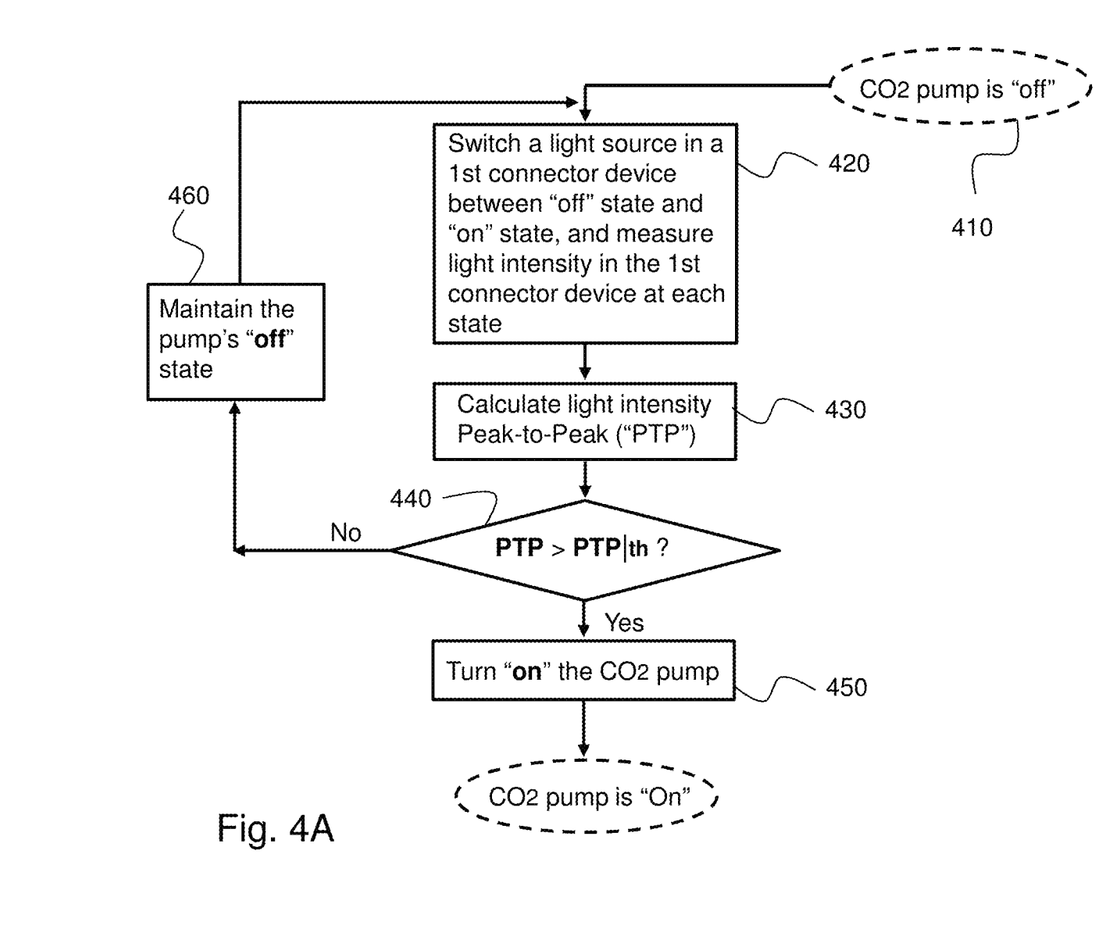
FIG. 4A is a flow diagram illustrating a method for activating a gas pump.

FIG. 4A is a method for detecting a connector assembly connection state required to switch a $CO_2$ pump "on", according to an example embodiment. At step 410, a $CO_2$ pump of a capnography system is in the "off" state. At step 420, a light source (e.g., LED) positioned in a capnograph connector (a "first" connector) is alternately switched between an "off" state and an "on" state and, using a light sensor that is embedded in or incorporated into the capnograph connector, light samples representing the light sensed by the light sensor at each light source operation state are collected. The light sensor in the capnograph connector senses light regardless of where the sensed light originates from, and thus it is unable to distinguish between light coming from different directions or light sources. That is, the light sensed inside the capnograph connector by the light sensor may be: light that is emitted by the LED of the capnograph connector device (i.e., 'internal' light) and reflected from a reflection surface of a tube connector (a second, or counterpart, connector) when the two connectors are properly (e.g., operationally) connected (engaged); or a 'partial' light reflection when the two connectors are poorly connected; or an ambient light (i.e., an 'external' light; e.g., daylight, artificial light; e.g., room light) when the two connectors are not connected at all (i.e., when they are completely disconnected).

When the two connectors are properly connected, the light sensed by the light sensor of the capnograph connector is expected to have high intensity when the LED (or another light source for that matter) in the capnograph connector is "on", and low to zero intensity when the LED is "off". When the two connectors are properly connected the intensity of the light sensed by the light sensor is expected to be low to zero because the second connector (the counterpart, or 'tube', connector) prevents (blocks) external light from entering through the connector assembly and reaching the light sensor (directly or indirectly). When the two connectors are properly connected (when the connector assembly is connection wise operational), the connector assembly may not be completely light-tight, meaning that spacings (air 'gaps') between the two connectors, even when properly engaged, may still enable some external light to reach the light sensor in the first connector (in the capnograph connector). Therefore, some external low light may still reach the light sensor when the two connectors are properly connected. To solve that problem, some light intensity margin can be used, which accommodates for such 'stray' light sensing. This light sensing technique may be utilized in determining whether the two connectors are properly connected, as described below in more detail.

At step 430, a light intensity Peak-to-Peak ("PTP") value is calculated from light samples that are/were taken both in the LED's "off" state and in the LED's "on" state. As described herein, low light intensities can be expected in the "off" state of the LED when the two connector devices are properly connected, and high light intensities can be expected in the "on" state of the LED when the connectors are properly connected. Referring again to step 420, a controller may control the light source to alternate between "off" state, in which the light source is shut down (not emitting light), and "on" state, in which the light source emits light. The difference between the intensity of the light sensed in the "off" state and the intensity of the light sensed in the "on" state (e.g., the PTP value) is expected to be large (corresponding to high PTP value) when the two connectors are properly connected. Therefore, if the PTP value is high (e.g., if it is greater than a predetermined threshold value (PTP|th)), the controller may determine that the two connectors are properly connected. Accordingly, at step 440 it is checked (e.g., by the controller) whether the PTP value is greater than the predetermined threshold value (PTP|th).

If it is determined at step 440 that the PTP value is greater than the predetermined threshold value (this condition is shown as "Yes" at step 440), then it is determined that the two connectors are properly connected. Therefore, at step 450 the $CO_2$ pump is turned "on". The $CO_2$ pump may run (be in the "on" state) for as long as the PTP value is greater than the predetermined threshold value, or until a user of the capnograph system (e.g., health care personnel) switches the $CO_2$ pump off, such as when the $CO_2$ monitoring procedure ends. However, if, for example, the controller, determines at step 440 that the PTP value is not greater than the predetermined threshold value (this condition is shown as "No" at step 440), the CO2 pump's "off" state is maintained (at 460).

As described herein, determining a proper (operational) connector connection only based on light intensity measurements may be problematic at times due to the adverse effect that electromagnetic interferences may have on the electrical circuits involved in the light intensity measurements and/or interpretation (such effect might cause the $CO_2$ pump to be erroneously turned "off" when it should stay running; i.e., "on"). Using pressure measurements that 'backup' the light-based connector disconnection decision solves that problem. It is noted that while light measurements are helpful in initiating pump activation, pressure measurements are used when the pump is "on" and the light readings indicate, potentially erroneously, disconnection or improper connection.

Figure 4B:
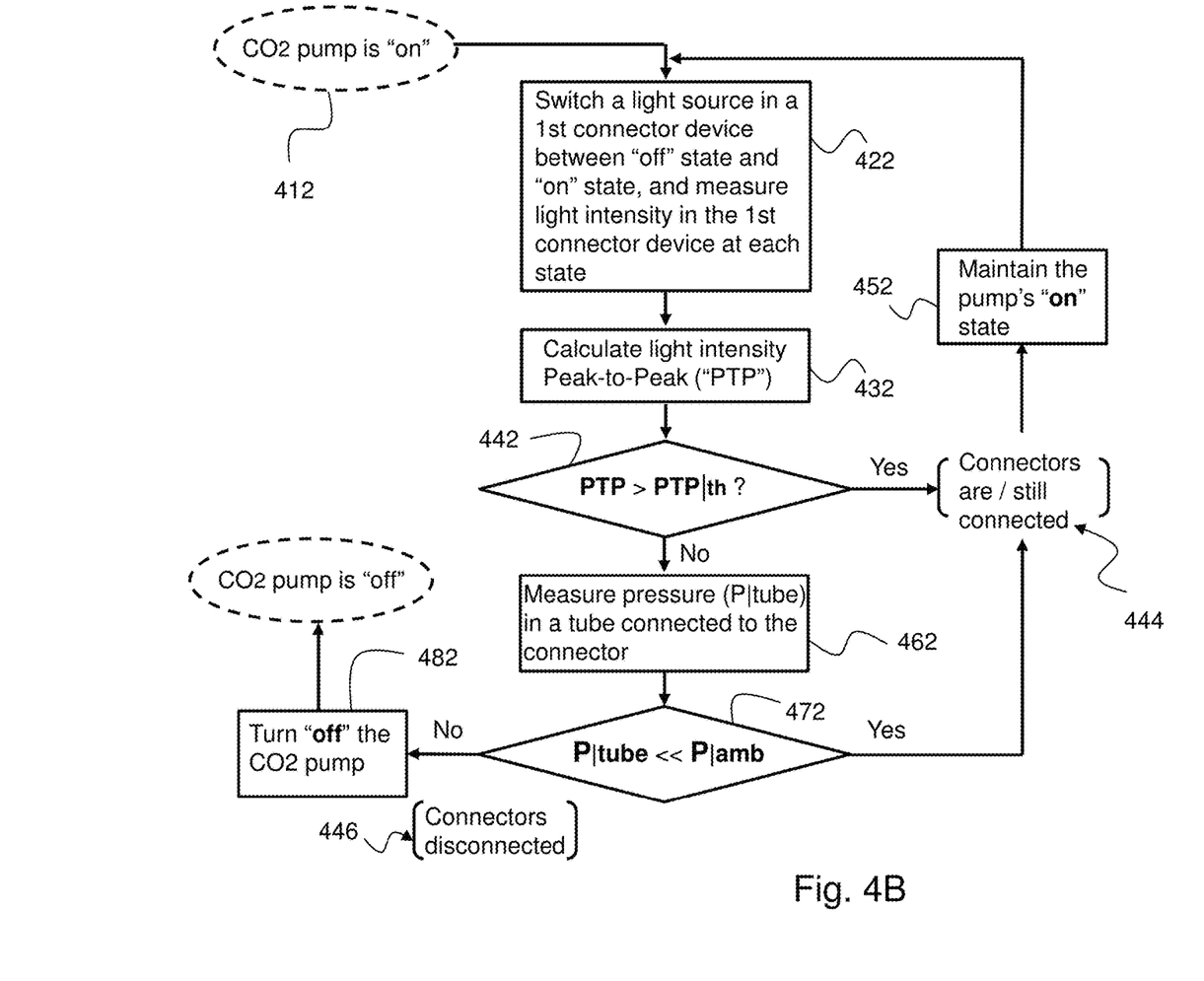
FIG. 4B is a flow diagram illustrating a method for deactivating a gas pump.

FIG. 4B is a method for detecting a connector assembly connection state required to switch a $CO_2$ pump "off", according to an example embodiment. At step 412, a $CO_2$ pump of a capnography system is in the "on" state. At step 422, a light source (e.g., LED) positioned in a first connector (e.g., in a capnograph connector) is alternately switched between an "off" state and an "on" state and, using a light sensor that is embedded in or incorporated into the first connector device, light samples representing the light sensed by the light sensor at each light source operation state are collected. As described herein, the light sensor in the first connector device does not distinguish between light coming from different light sources. That is, the light sensed inside the first connector device may be: light that is emitted by the LED of the first connector device and reflected from a reflection surface in or on a second connector (e.g., a 'tube', or counterpart, connector) when the two connectors are properly connected; or a 'partial' light reflection when the two connectors are poorly connected; or an ambient light when the two connectors are not connected at all (i.e., when they are completely disconnected).

As described herein (for similar reasons), when the two connectors are properly connected, the light sensed by the light sensor of the first connector device is expected to have high intensity when the LED (or another light source for that matter) in the first connector device is "on", and low to zero intensity when the LED is "off".

At step 432, a light intensity PTP value is calculated from light samples that are/were taken both in the LED's "off" state and in the LED's "on" state. As described herein, low light intensities can be expected in the "off" state of the LED when the two connector devices are properly connected; and high light intensities can be expected in the "on" state of the LED when the connectors are properly connected. Referring again to step 422, a controller may control the light source to alternate between "off" state, in which the light source is shut down (not emitting light), and "on" state, in which the light source emits light, and the difference between the intensity of the light sensed in the "off" state and the intensity of the light sensed in the "on" state (e.g., the PTP value) is expected to be large (corresponding to high PTP value) when the two connectors are properly connected. Therefore, if the PTP value is high (e.g., if it is greater than a predetermined threshold value (PTP|th)), the controller may determine that the two connectors are properly connected. Accordingly, at step 442 it is checked (e.g., by the controller) whether the PTP value is greater than the predetermined threshold value (PTP|th).

If it is determined at step 442 that the PTP value is greater than the predetermined threshold value (this condition is shown as "Yes" at step 442), then it is determined (e.g., by the controller) that the two connectors are (or are still) properly connected (at 444). Therefore, at step 452, the $CO_2$ pump's "on" state is maintained. The $CO_2$ pump may run (be in the "on" state) for as long as the PTP value is greater than the predetermined threshold value, or until a user of the capnograph system (e.g., health care personnel) intentionally switches the $CO_2$ pump off, such as when the $CO_2$ monitoring procedure ends. However, if the controller (for example) determines at step 442 that the PTP value is not greater than the predetermined threshold value (this condition is shown as "No" at step 442), it may be that the two connectors are improperly connected or completely disconnected, or that the light samples, processing or interpretation has been compromised (e.g., adversely affected) by electromagnetic interferences (or by some other interference; e.g., by mechanical interference). Initially, if the PTP value is not greater than the predetermined threshold value, the $CO_2$ pump should normally be switched off. However, if the cause to the low PTP value ('low value'—a value not greater than the predetermined threshold value) is an electromagnetic interference (or another type of interference), the CO2 pump's "on" state is maintained, and the connector assembly's connection state ("proper connection", "improper connection", "complete disconnection") is reevaluated by using another, orthogonal, parameter. The connectors' connection state reevaluation process is referred to herein as a "corroboration phase".

The corroboration phase includes steps 462 and 472. The corroboration phase, or any step thereof, may include additional steps, for example steps involving manipulation of pressure measurements/samples in any way that can result in enhanced accuracy, etc. The corroboration phase, which uses pressure as an example parameter that is orthogonal to the light samples, utilizes the fact that when the $CO_2$ pump draws $CO_2$ from (through) a gas sampling line ("GSL"), a vacuum is created in the GSL; that is, the gas pressure in the GSL gets lower than the ambient/atmospheric pressure (lower than the air/gas pressure just outside the GSL) (the GSL includes two gas tubes and the two connectors, all of which are in gas flow communication.) The amount ('depth') of vacuum helps determine whether the GSL leaks due, for example, to the two connector devices being improperly connected or completely disconnected. In general, the better the connectors are connected, the more airtight the connection and, consequently, the 'deeper' the vacuum (the lower the pressure in the GSL relative to the air pressure outside the GSL). Accordingly, if the vacuum is deep 'enough'; that is, if the pressure difference between the (low) pressure in the GSL and the pressure outside the GSL is greater than a threshold value (which may depend, among other things, on the internal diameter and length of the gas tube of the GSL), a controller may determine that the two connectors are properly connected, hence operational.

At step 462, the pressure (P|tube) in the GSL is measured, and at step 472 it is checked, for example by the controller, whether the pressure P|tube is 'significantly' lower than P|amb (the ambient pressure just outside the tube). Vacuum produced in the GSL by the $CO_2$ pump is measured as a pressure difference between P|amb and P|tube (the lower P|tube relative to P|amb, the greater the vacuum). A pressure difference threshold value Delta.P|th (where Delta.P|th=P|amb−P|tube) may be used to determine when the vacuum is deep enough (deep enough to indicate proper connection of the two connectors); that is, when the pressure difference P|amb−P|tube indicates a proper vacuum in the GSL, hence a proper connectors' connection.

If, per the pressure difference threshold value Delta.P|th, it is determined at step 472, for example by the controller, that the value of P|tube is not low enough relative to the ambient pressure P|amb (this condition is shown as "No" at step 472), then it is determined (at 446) that the two connectors are disconnected, or that they are improperly connected, which is in agreement with (i.e., corroborating) the initial disconnection (or poor connection) decision arrived at (e.g., by the controller) by using the light samples PTP value. Therefore, at step 482 the CO2 pump is turned "off".

However, if, per the pressure difference threshold value Delta.P|th, it is determined at step 472 that the value of P|tube is low enough relative to the ambient pressure P|amb (this condition is shown as "Yes" at step 472), then it is determined (at 444), for example by the controller, that the two connectors are indeed connected, contrary to the light PTP value indication. Therefore, at step 452 the $CO_2$ pump remains in the "on" state even though the light PTP intensity value checked at step 442 indicates a connector's disconnection.

Figure 5:
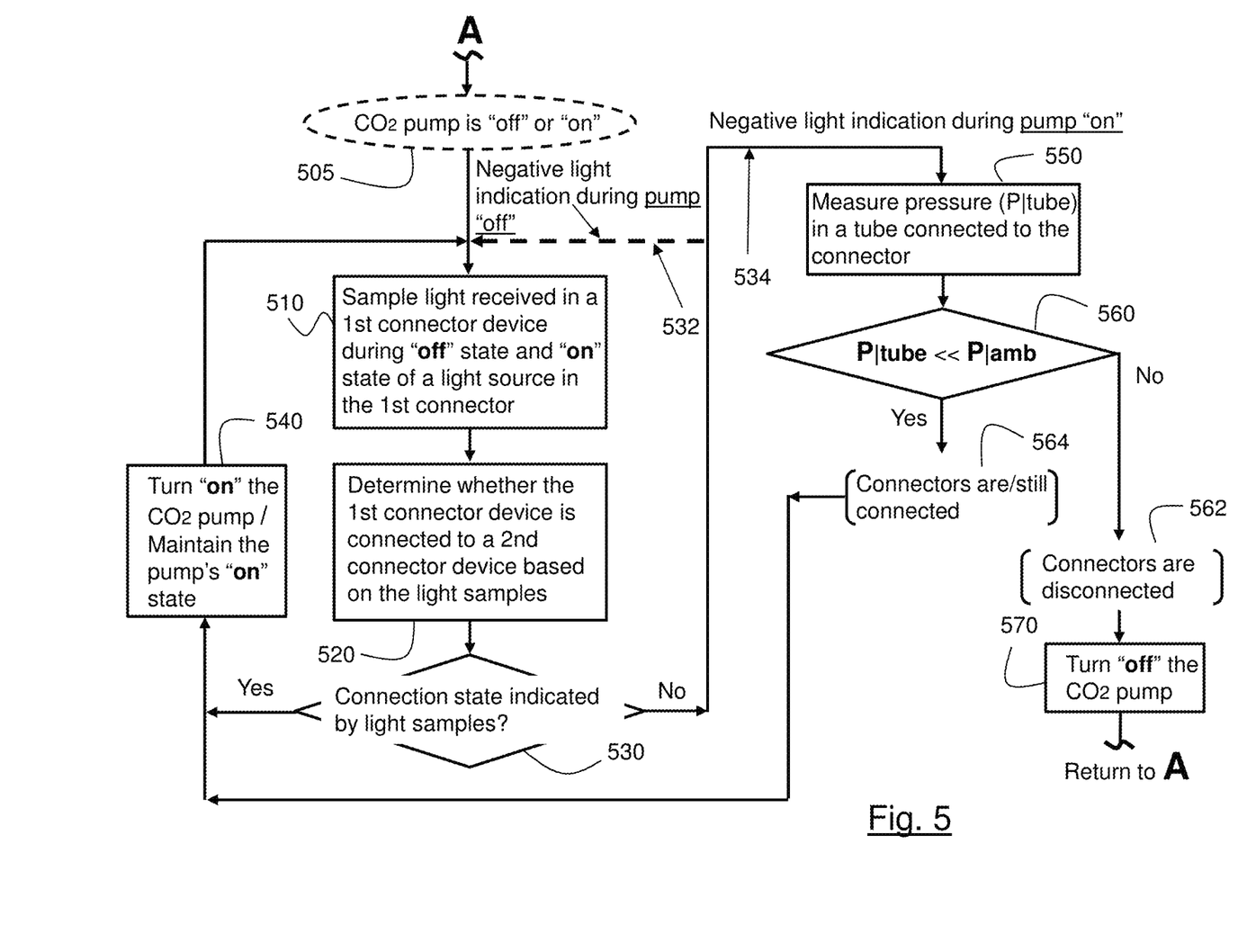
FIG. 5 is a flow diagram illustrating a method for activating and deactivating a gas pump.

FIG. 5 shows a method for detecting a connector disconnection (or poor connection) state according to another example embodiment. The process in FIG. 5 can start with the $CO_2$ pump being either in the "off" state or in the "on" state, as shown at 505. At step 510, a light source that is positioned in a first connector (e.g., in a capnograph connector) may alternately be switched "on" and "off"; and light sensed by a light sensor that is embedded in the first connector device may be sampled one or more times during each state of the light source (Features described in connection with step 510, or part thereof, may be implemented as part of, or be applicable also to, step 420 of FIG. 4A and/or step 422 of FIG. 4B, and vice versa. Steps 510, 420 and 422 may be analogous).

When a second connector (e.g., a tube, or counterpart, connector) including a light reflecting surface is connected to the first connector device, it is expected that light originating from the light source embedded in the first connector device will be reflected from the light reflecting surface embedded in the second connector device and be sensed by the light sensor in the first connector device. Accordingly, at step 520, it is determined (for example by a controller), based on or from light samples taken during both light source "on" state and "off" state, whether the first connector device is properly connected to the second connector device. For example, light intensity measurements taken during "on" state and light intensity measurements taken during "off" state may be used to calculate one or more light intensity PTP values, and the determination as to whether the two connector devices are properly connected or not may be based on, for example, computation and manipulation of multiple PTP values. For example, an average value of subsequent PTP values may be calculated and used to determine whether the two connectors are properly connected.

At step 530, it is checked whether a proper connection of the two connector devices is indicated by the light samples. Indication of proper connector connection may be obtained, for example, by computing, from light samples, a single light PTP value (for example a light PTP value per unit of time; e.g., computing a PTP value once every couple of seconds, once every minute, etc.), or by computing, from light samples, a plurality of PTP values (and computing a PTP value; e.g., an average PTP value, representing these PTP values), etc. (features described in connection with steps 520-530 of FIG. 5 may be implemented as part of, or be applicable also to, steps 430-440 of FIG. 4A and/or to steps 432-442 of FIG. 4B, and vice versa. The combination of steps 520-530 (or some features of one step or both steps), the combination of steps 430-440 (or some features of one step or both steps) and the combination of steps 432-442 (or some features of one step or both steps) may be analogous).

If a connection state is indicated by the light samples (this condition is shown as "Yes" at step 530), then, at step 540, the $CO_2$ pump is switched "on" if it was in the "off" state, or (if the pump is already "on") its "on" state is maintained. However, if the light samples provide an indication that the two connectors are poorly connected or completely disconnected (this condition is shown as "No" at step 530), selection of the next steps, or next 'path', depends on whether the $CO_2$ pump is currently "off" (deactivated) or already "on" (active):

if the $CO_2$ pump is currently "off" (cf. path 532), the light-based decision steps (e.g., steps 510, 520 and 530) are repeated because, as described herein, activation of the $CO_2$ pump (transitioning the pump from "off" state to "on" state) requires that light samples indicate a proper connection of the two connectors; However, if the $CO_2$ pump is already/currently "on" (cf. path 534), a corroboration phase/procedure is additionally (e.g., subsequently) performed in order to recheck whether the connector devices are disconnected or improperly connected (if disconnection/improper connection of the two connectors is confirmed by pressure measurement(s), the $CO_2$ pump is deactivated; i.e., switched off). That is, gas pressure in the GSL is measured to corroborate (or refute) the light-based disconnection, or improper connection, indication. The corroboration phase/procedure may include steps 550 and 560 (features described in connection with steps 550-560 of FIG. 5 may be implemented as part of, or be applicable also to, steps 462-472 of FIG. 4B, and vice versa. Steps 550-560 (or some features thereof) and steps 462-472 (or some features thereof) may be analogous).

At step 550, the pressure (P|tube) in the GSL connected is measured, and, at step 560, it is checked, for example by a controller, whether the pressure in the GSL, P|tube, is low enough relative to P|amb (the ambient pressure just outside the tube or GSL). A pressure difference threshold value Delta.P|th (where Delta.P|th=P|amb−P|tube) may be used to determine when the pressure difference P|amb−P|tube indicates a proper vacuum in the GSL, hence a proper connector connection.

If, per the threshold value Delta.P|th, it is determined at step 560 that the value of P|tube is not low enough relative to P|amb (this condition is shown as "No" at step 560), it is determined, for example by the controller, that the two connectors are disconnected or are improperly connected (cf. 562). Therefore, at step 570 the $CO_2$ pump is turned "off", and steps 510, 520 and 530 are repeated, now with the pump in the "off" state (the pump's "off" state is maintained until light samples indicate that the two connectors are properly connected).

However, if, per the threshold value Delta.P|th, it is determined at step 560, for example by the controller, that the value of P|tube is low enough relative to P|amb (this condition is shown as "Yes" at step 560), then it is determined (cf. 564), for example by the controller, that the two connectors are connected, or still connected. Therefore, at step 540 the pump remains in the "on" state even though the light samples collected at step 510 indicate improper connection or complete disconnection of the two connectors, and steps 510 through 530 are repeated with the pump in the "on" state. The pump remains in the "on" state until both light samples (per step 530) and pressure measurement(s) (per step 560) indicate that the connector devices are disconnected or improperly connected.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Although portions of the discussions herein refer to a gas sampling system and to a gas sampling line for sampling and analyzing $CO_2$, the present invention is not limited in this regard; and the invention, or aspects thereof, may be applicable to other gas sampling systems. Those skilled in the art of, for example, gas analysis will understand how to apply the invention to other types of gas analyzing systems, and will readily appreciate that various changes, variations, and modifications can be made to accommodate for differences between such systems without departing from the scope of the invention.

What is claimed is:

1. A capnograph module for a capnograph system, the capnograph module comprising:
   a capnograph connector configured to receive $CO_2$ samples from a gas sampling line via a gas sampling line connector, said capnograph connector comprising a light source and a light sensor;
   a pump configured to draw $CO_2$ samples via the capnograph connector for analysis;
   a pressure sensor configured to sense pressure in the gas sampling line; and
   a controller configured to control operation of the pump and light source and to measure intensity of light sensed by the light sensor,
   wherein the controller is configured to:
   when the pump is on/active, sample light while switching the light source "on" and "off"; and
   when light samples indicate misconnection between the capnograph connector and the gas sampling line connector:
   (i) switch the pump off when a pressure measured in the gas sampling line corroborates the light samples misconnection indication; and
   (ii) maintain the pump in the on state if the measured pressure refutes the light samples misconnection indication.

2. The capnograph module as in claim 1, wherein the controller is further configured to:
   when the pump is off/inactive, sample light while switching the light source "on" and "off"; and
   when light samples indicate a proper connection of the capnograph connector and the gas sampling line connector, switch the pump on.

3. The capnograph module as in claim 1, further comprising a light control circuit configured to enable switching the light source "on" and "off" and to receive a signal representing light that is sensed by the light sensor.

4. The capnograph module as in claim 3, wherein the controller is configured to alternately switch the light source between "on" state and "off" state and, using the light sensor, to sense light one or more times during an "on" state and during an "off" state.

5. The capnograph module as in claim 1, wherein the light sensed by the light sensor is any one, or a combination, of:
   (i) light originating from the light source and reflected, at least partly, by a light reflecting surface of the gas sampling line connector; and
   (ii) light which is not originating from the light source.

6. The capnograph module as in claim 1, wherein the pump is connected to the capnograph connector by a pump tube.

7. The capnograph module as in claim 6, wherein the pressure sensor is in fluid flow communication with the pump tube to sense pressure in the gas sampling line.

8. The capnograph module as in claim 1, wherein the controller is configured to calculate a pressure threshold value to determine corroboration or refutation of a connector's misconnection indication.

9. The capnograph module as in claim 1, further comprising a gas analyzer.

10. A gas analyzing module for a gas analyzing system, the gas analyzing module comprising:
    a gas connector configured to receive gas samples from a gas sampling line via a gas sampling line connector, said gas connector comprising a light source and a light sensor;
    a pump configured to draw gas samples via the gas connector for analysis;
    a pressure sensor configured to sense pressure in the gas sampling line; and
    a controller configured to control operation of the pump and light source and to measure intensity of light sensed by the light sensor,
    wherein the controller is configured to:
    when the pump is on/active, sample light while switching the light source "on" and "off"; and
    when light samples indicate misconnection between the gas connector and the gas sampling line connector:
    (i) switch the pump off when a pressure measured in the gas sampling line corroborates the light samples misconnection indication; and
    (ii) maintain the pump in the on state if the measured pressure refutes the light samples misconnection indication.

11. The gas analyzing module as in claim 10, wherein the controller is further configured to:
    when the pump is off/inactive, sample light while switching the light source "on" and "off"; and
    when light samples indicate a proper connection of the gas connector and the gas sampling line connector, switch the pump on.

12. The gas analyzing module in claim 10, wherein the gas analyzing system is a $CO_2$ analyzing system.

13. A capnograph system, comprising:
    a $CO_2$ analyzer; and
    a capnograph module, comprising:
    a capnograph connector configured to receive $CO_2$ samples from a gas sampling line via a gas sampling line connector, said capnograph connector comprising a light source and a light sensor;
    a pump configured to draw $CO_2$ samples via the capnograph connector for analysis;
    a pressure sensor configured to sense pressure in the gas sampling line; and
    a controller configured to control operation of the pump and light source and to measure intensity of light sensed by the light sensor,
    wherein the controller is configured to:
    when the pump is on/active, sample light while switching the light source "on" and "off"; and
    when light samples indicate misconnection between the capnograph connector and the gas sampling line connector:
    switch the pump off when a pressure measured in the gas sampling line corroborates the light samples misconnection indication; and maintain the pump in the on state when the measured pressure refutes the light samples misconnection indication.

14. A method, comprising:
providing a capnograph connector configured to receive $CO_2$ samples from a gas sampling line via a gas sampling line connector, said capnograph connector comprising a light source and a light sensor;
providing a pump configured to draw $CO_2$ samples via the capnograph connector for analysis; and
providing a controller configured as a $CO_2$ analyzing system to control operation of the pump and light source and to measure intensity of light sensed by the light sensor, further comprising:
when the pump is on/active,
sampling light while switching the light source "on" and "off", and when light samples indicate misconnection between the capnograph connector and the gas sampling line connector; and
switching the $CO_2$ pump off when a pressure measured in the gas sampling line corroborates the light samples misconnection indication; or
maintaining the $CO_2$ pump in the on state when the measured pressure refutes the light samples misconnection indication.

15. The method as in claim 14, comprising:
when the pump is off/inactive,
sampling light while switching the light source "on" and "off"; and
when light samples indicate a proper connection of the capnograph connector and the gas sampling line connector, switching the pump on.

16. The method as in claim 15, wherein indicating misconnection or proper connection of the capnograph connector and the gas sampling line connector based on light samples comprises calculating one or more light intensity peak-to-peak (PTP) values from light samples taken in the light source "off" state and in the light source "on" state.

17. The method as in claim 16, wherein a peak-to-peak (PTP) value is calculated from one or more light intensity values obtained during an "on" period of the light source and from one or more light intensity values obtained during an a preceding, or succeeding, "off" period of the light source.

18. The method as in claim 16, comprising calculating a predetermined number of PTP values per unit of time, or per a predetermined time interval or on/off cycle, or once in a while, wherein an on/off cycle comprises an "on" period of the light source and a preceding, or succeeding, "off" period of the light source.

19. The method as in claim 16, comprising calculating an average PTP value and determining either misconnection or proper connection of the capnograph connector and the gas sampling line connector.

20. The method as in claim 14, wherein switching the light source "on" and "off" comprises alternately switching the light source between "on" state and "off" state.

21. A gas analyzing module for a gas system, the gas analyzing module comprising:
a gas connector configured to receive gas samples from a gas sampling line via a gas sampling line connector, said gas connector comprising a connection detection mechanism (CDM) configured to detect connection of the gas connector and the gas sampling line connector;
a pressure sensor configured to sense pressure in the gas sampling line;
a pump configured to draw gas samples via the gas connector for analysis; and
a controller configured to control operation of the pump and to determine, based on a signal output by the CDM, connection or misconnection of the gas connector and the gas sampling line connector,
wherein the controller is configured to:
when the pump is on/active and when the CDM signal indicates misconnection between the gas connector and the gas sampling line connector:
(i) switch the pump off when a pressure measured in the gas sampling line corroborates the CDM's misconnection indication; and
(ii) maintain the pump in the on state if the measured pressure refutes the CDM's misconnection indication.

22. The gas analyzing module as in claim 21, wherein the controller is further configured to:
when the pump is off/inactive, read the CDM signal and, if the CDM signal indicates a proper connection of the gas connector and the gas sampling line connector, switch the pump on.

23. The gas analyzing module as in claim 21, further comprising a pump tube, said pump tube connecting the pump to the gas connector.

24. The gas analyzing module as in claim 23, wherein the pressure sensor is in fluid flow communication with the pump tube to sense pressure in the gas sampling line.

25. The gas analyzing module as in claim 21, wherein the controller is configured to calculate a pressure threshold value to determine corroboration, or refutation, of a connectors misconnection indication.

26. The gas analyzing module as in claim 21, further comprising a gas analyzer.

27. The gas analyzing module as in claim 21, wherein the gas analyzing module is a capnograph module configured for capnography.

28. The gas analyzing module as in claim 21, wherein the connection detection mechanism (CDM) comprises a light source and a light sensor.

* * * * *